US010195397B2

(12) United States Patent
Knutson et al.

(10) Patent No.: US 10,195,397 B2
(45) Date of Patent: Feb. 5, 2019

(54) ACTUATOR RESTRAINING ASSEMBLY FOR MEDICAL DEVICE

(71) Applicant: St. Jude Medical, Cardiology Division, Inc., St. Paul, MN (US)

(72) Inventors: Anthony Knutson, St. Paul, MN (US); Michael Bowers, Edina, MN (US); Stephan P. Miller, Vadnais Heights, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 451 days.

(21) Appl. No.: 14/573,115

(22) Filed: Dec. 17, 2014

(65) Prior Publication Data

US 2015/0174369 A1 Jun. 25, 2015

Related U.S. Application Data

(60) Provisional application No. 61/919,095, filed on Dec. 30, 2013.

(51) Int. Cl.
*A61M 31/00* (2006.01)
*A61M 25/01* (2006.01)

(52) U.S. Cl.
CPC .... *A61M 25/0147* (2013.01); *A61M 25/0136* (2013.01); *A61M 2205/582* (2013.01)

(58) Field of Classification Search
CPC .......... A61M 25/0147; A61M 25/0136; A61M 2205/582
USPC ...................................... 604/95.04
See application file for complete search history.

(56) References Cited

U.S. PATENT DOCUMENTS 7,722,302 B2 * 5/2010 Mynhier ............... F16B 31/043
411/14.5
7,905,864 B2 * 3/2011 Ponzi ................. A61B 18/1492
604/164.02

FOREIGN PATENT DOCUMENTS

| EP | 1905376 | 4/2008 |
|---|---|---|
| JP | 2001-178828 | 7/2001 |
| JP | 2007-524439 | 8/2007 |
| JP | 201155848 | 3/2011 |
| JP | 2011-234977 | 11/2011 |

(Continued)

OTHER PUBLICATIONS

An International Search Report for PCT Application No. PCT/US2014/070762, dated Mar. 20, 2015, 5 pgs.

*Primary Examiner* — Phillip Gray
(74) *Attorney, Agent, or Firm* — Wiley Rein LLP

(57) ABSTRACT

A medical device includes an elongate body having a proximal end and a deflectable distal region, a handle coupled to the proximal end, an actuator movable relative to the handle, and a resistance assembly adjacent the actuator. The resistance assembly exerts a force on the actuator that varies according to a direction in which the actuator is moving relative to the handle. For example, the resistance assembly can exert a lower (or zero) force when the actuator is moving relative to the handle in a direction that effects deflection of the distal region of the elongate body from neutral and higher when the actuator is moving relative to the handle in a direction that effects return of the distal region of the elongate body towards neutral. The resistance assembly can also include materials that exhibit anisotropic frictional properties and/or have surface finishes or treatments that yield directionally-dependent frictional forces.

22 Claims, 2 Drawing Sheets

(56) References Cited

FOREIGN PATENT DOCUMENTS

| WO | 93/004724 | 3/1993 |
| WO | 2011/142142 | 11/2011 |

* cited by examiner

ACTUATOR RESTRAINING ASSEMBLY FOR MEDICAL DEVICE

CROSS-REFERENCE TO RELATED APPLICATIONS

This application claims the benefit of U.S. provisional application No. 61/919,095, filed 20 Dec. 2013, which is hereby incorporated by reference as though fully set forth herein.

BACKGROUND

The instant disclosure relates to actuators for medical devices. In particular, the instant disclosure relates to restraining assemblies to hold such actuators in particular positions and/or to make it easier to move such actuators in one direction versus another.

Catheters, including electrophysiology catheters, are used in a variety of diagnostic and therapeutic procedures to diagnose and/or treat conditions such as atrial arrhythmias. Typically, a catheter is deployed and manipulated through a patient's vasculature to the intended site, such as a site within a patient's heart.

To position a catheter within the body at a desired site, some type of navigation must be used, such as using mechanical steering features incorporated into the catheter (or an introducer sheath, which itself is a type of catheter-like medical device). In some examples, medical personnel may manually manipulate and/or operate the catheter using these mechanical steering features.

In order to facilitate the advancement of a catheter through a patient's vasculature, the simultaneous application of torque at the proximal end of the catheter and the ability to selectively deflect the distal tip of the catheter in a desired direction can permit medical personnel to adjust the direction of the advancement of the distal end of the catheter and to selectively position the distal portion of the catheter during a procedure. The proximal end of the catheter can be manipulated to guide the catheter through the patient's vasculature. The distal tip of the catheter can be deflected by a pull wire or other tension member attached or anchored at the distal end of the catheter and extending proximally to an actuator in a control handle that controls the application of tension on the pull wire.

BRIEF SUMMARY

It is desirable to minimize the force a practitioner must apply to the actuator in order to effect deflection of the distal tip of the catheter, yet provide sufficient friction against reverse actuator movement (that is, against movement of the actuator in order to effect return of the distal tip of the catheter towards a neutral position).

Disclosed herein is a medical device including: a body having a proximal end and a deflectable distal region; a handle attached to the proximal end of the body, the handle including an actuator movable relative to the handle along a longitudinal axis thereof; and a resistance assembly positioned adjacent the actuator, wherein the resistance assembly exerts a first frictional force on the actuator when the actuator is moved in a first direction along the longitudinal axis of the handle and a second frictional force on the actuator when the actuator is moved in a second direction along the longitudinal axis of the handle, wherein the second direction is opposite the first direction, and wherein the second frictional force is greater than the first frictional force.

In certain aspects, the resistance assembly can include an annular friction assembly positioned around the actuator. The annular friction assembly can be made of a material having anisotropic frictional properties. Alternatively or additionally, the annular friction assembly can include a surface finish or treatment that yields directionally-dependent frictional forces.

The annular friction assembly can include a compression ring having a chamfered first surface and a second surface opposite the first surface, wherein the first surface is oriented in the first direction.

In other embodiments, the annular friction assembly includes: an annular disk having a beveled first surface and a second surface opposite the first surface, wherein the first surface is oriented in the first direction; and an o-ring positioned adjacent the first surface of the annular disk. The o-ring can have a non-circular cross-sectional shape.

It is contemplated that the resistance assembly can also include a constraining housing, wherein the annular friction assembly is positioned within the constraining housing.

A pull wire can extend through the body and can be coupled to the distal region of the body to effect deflection thereof, such that moving the actuator in the first direction effects deflection of the body from neutral in a first deflection direction. Moving the actuator in the second direction can effect a return of the body to neutral or effect a deflection of the body from neutral in a second deflection direction.

Also disclosed herein is a medical device including: an elongate body having a proximal end and a deflectable distal region; a handle coupled to the proximal end of the elongate body and including an actuator movable relative to the handle; and a resistance assembly adjacent the actuator, wherein the resistance assembly is configured to exert a force on the actuator that varies according to a direction in which the actuator is moving relative to the handle.

In certain aspects, the force exerted by the resistance assembly is lower (and can be at or near zero) when the actuator is moving relative to the handle in a direction that effects deflection of the distal region of the elongate body from neutral and higher when the actuator is moving relative to the handle in a direction that effects return of the distal region of the elongate body towards neutral.

In other aspects, the force exerted by the resistance assembly is lower (and can be at or near zero) when the actuator is moving relative to the handle in a direction that effects deflection of the distal region of the elongate body from neutral in a first deflection direction and higher when the actuator is moving relative to the handle in a direction that effects deflection of the distal region of the elongate body from neutral in a second deflection direction opposite the first deflection direction.

The resistance assembly can include a member made of a material having anisotropic frictional properties. Alternatively or additionally, the resistance assembly can include a member having a surface treatment or finish that yields directionally-dependent frictional forces (e.g., a fish scale pattern). As a further alternative or addition, the surface treatment or finish can be on the actuator. If on the resistance assembly, the surface treatment or finish can be on the surface that faces the actuator; if on the actuator, the surface treatment or finish can be on the surface that faces the resistance assembly.

The resistance assembly can include an annular member positioned around the actuator, wherein the annular member includes a first surface and a second surface, and wherein the first surface of the annular member includes a cavity. The resistance assembly can further include a compressible member positioned around the actuator adjacent the first surface of the annular member and within the cavity, wherein movement of the actuator in a first direction separates the compressible member from the first surface of the annular member, thereby minimizing resistance to movement of the actuator in the first direction, and wherein movement of the actuator in a second direction opposite the first direction drives the compressible member against the first surface of the annular member, thereby maximizing resistance to movement of the actuator in the second direction.

In another embodiment, a resistance assembly to impart resistance to movement of an actuator for a medical device includes: a constraining housing; and an annular friction assembly positioned within the housing, wherein a lower (including at or near zero) force is required to pass the actuator through the annular friction assembly in a first direction than to pass the actuator through the annular friction assembly in the second direction.

The annular friction assembly can include a material having anisotropic frictional properties. Alternatively or additionally, it can have a surface treatment or finish that yields directionally-dependent frictional forces.

The annular friction assembly can include an annular compression ring having a first surface and a second surface, wherein the first surface includes a cavity such that there is greater distance between the first surface of the compression ring and the constraining housing than between the second surface of the compression ring and the constraining housing.

In another aspect, the annular friction assembly includes: an annular disk having a first surface and a second surface, wherein the first surface includes a wedge-shaped portion; and a compressible member riding on the wedge-shaped portion, such that, when the actuator is passed through the annular friction assembly in the first direction, the compressible member separates from the annular disk, and when the actuator is passed through the annular friction assembly in the second direction, the compressible member is wedged between the actuator and the annular disk. The compressible member can be an o-ring.

The foregoing and other aspects, features, details, utilities, and advantages of the present invention will be apparent from reading the following description and claims, and from reviewing the accompanying drawings.

DETAILED DESCRIPTION

Figure 1:
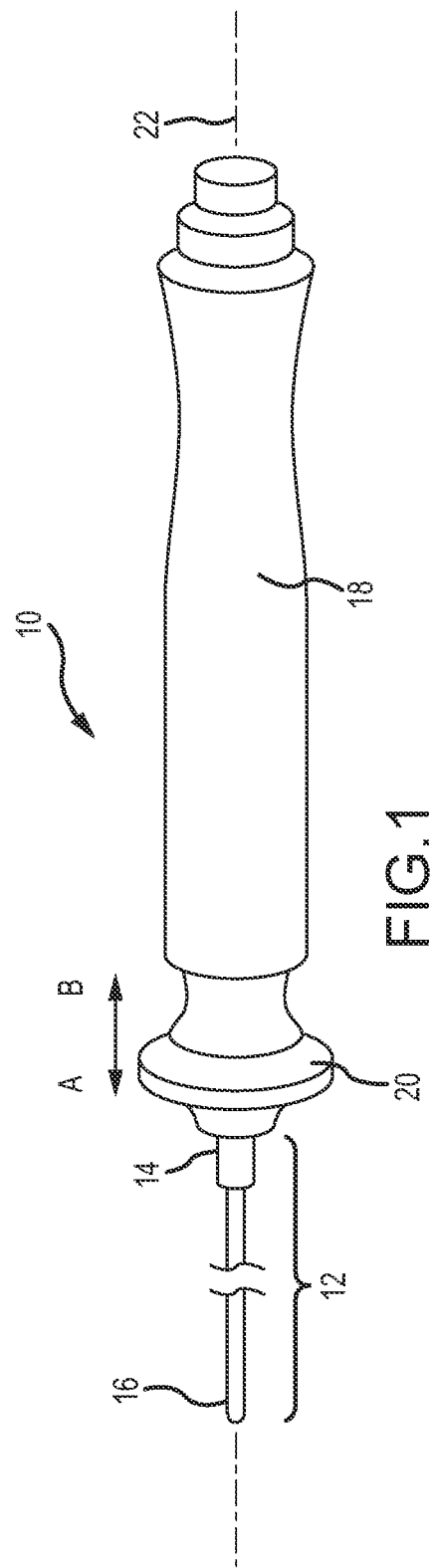
FIG. 1 depicts a plunger-type catheter.

FIG. 1 depicts a plunger-type catheter 10 in an undeflected, or neutral, position. Catheter 10 generally includes an elongate body 12, having a proximal end 14 and a deflectable distal region 16, and a handle 18 attached to proximal end 14 of body 12. Handle 18 includes an actuator 20. As depicted in FIG. 1, actuator 20 is a plunger that is moveable relative to handle 18 along a longitudinal axis 22 of handle 18 in a first direction along arrow A (e.g., distally) that effects deflection of distal region 16 from the neutral position, as well as in a second, opposite direction along arrow B (e.g., proximally) that effects return of distal region 16 towards the neutral position. For example, catheter 10 can be of the type disclosed in U.S. provisional application No. 61/884,897, filed 30 Sep. 2013, which is hereby incorporated by reference as though fully set forth herein.

Figure 2:
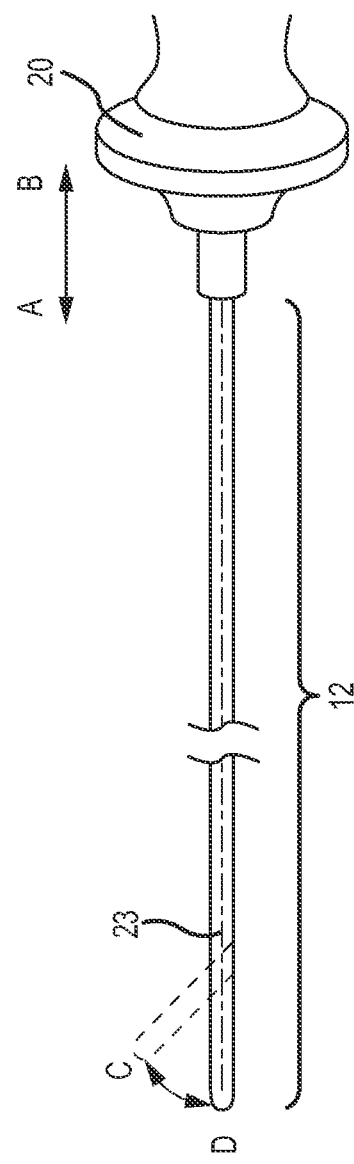
FIG. 2 depicts the use of a pull wire to deflect the distal end of the plunger-type catheter illustrated in FIG. 1.

FIG. 2 depicts additional components of catheter 10, namely including a pull wire 23 that extends through body 12. Pull wire is coupled to distal region 16 of body 12, such that movement of actuator 20 in the first direction along arrow A effects deflection of distal region 16 from the neutral position along a first deflection direction (e.g., arrow C), and such that movement of actuator 20 in the second direction along arrow B effects return of distal region 16 towards the neutral position (e.g., along arrow D). Insofar as the ordinarily skilled artisan will appreciate the use of pull wires in a catheter, a detailed explanation of this aspect of the disclosure need not be, and therefore is not, provided herein.

For purposes of explanation, various embodiments are disclosed herein with reference to a unidirectional catheter. It should be recognized, however, that the disclosed principles are equally applicable in other contexts, including, without limitation, bidirectional catheters. Thus, for example, movement of actuator 20 in the first direction along arrow A could effect deflection of distal region 16 from the neutral position in a first deflection direction (e.g., arrow C in FIG. 2), while movement of actuator 20 in the second direction could effect deflection of distal region 16 from the neutral position in a second deflection direction, with both the first deflection direction and second deflection direction lying in the same plane.

Handle 18 also includes a resistance assembly that operates to make it relatively easier for the practitioner to move actuator 20 in the first direction along arrow A and relatively harder for the practitioner to move actuator 20 in the second direction along arrow B, no matter what sort of movement of distal region 16 is effected thereby (e.g., whether deflection from neutral or return to neutral). Typically, the force exerted by the resistance assembly is a frictional force arising between actuator 20 and the resistance assembly. That is, the resistance assembly provides a frictional resistance against the movement of actuator 20 relative to handle 18, which frictional resistance differs depending on the direction in which actuator 20 is moving.

Figure 3:
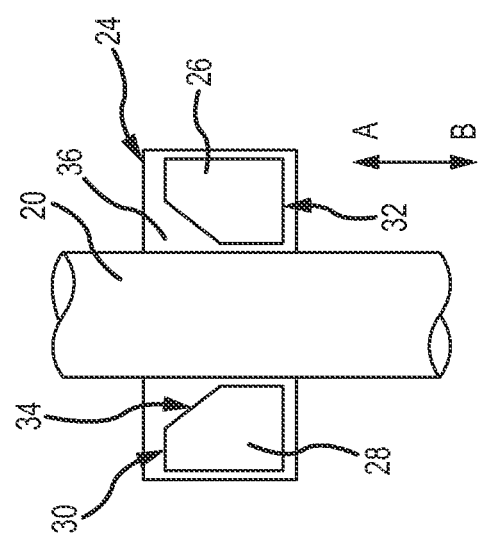
FIG. 3 is a cross-sectional view of a first exemplary embodiment of a resistance assembly according to the teachings herein.

FIG. 3 depicts a first exemplary resistance assembly 24 positioned adjacent actuator 20 and including a constraining housing 26 and a compression ring 28 positioned around actuator 20. Compression ring 28 includes a first surface 30 and a second, opposite surface 32. First surface 30 includes a chamfer 34, while second surface 32 is generally flat (that is, it generally follows the profile of constraining housing 26). Chamfer 34 forms a cavity 36 in first surface 30, such that there is a greater distance between first surface 30 and constraining housing 26 than between second surface 32 and constraining housing 26.

First surface 30 is oriented in the direction where the lower resistance to movement of actuator 20 is desired—for example, in the first (e.g., distal) direction that effects deflection of distal region 16 from neutral. Thus, as actuator 20 is driven in the first direction along arrow A, compression ring 28 deforms into the space created by chamfer 34 (i.e., cavity 36), thereby reducing both the normal force that compression ring 28 exerts on actuator 20 and the frictional resistance to movement of actuator 20 in the first direction. Conversely, when actuator 20 is driven in the second direction along arrow B, compression ring 28 is driven against constraining housing 26, increasing both the normal force that compression ring 28 exerts on actuator 20 and the frictional resistance to movement of actuator 20 in the second direction. As a result, it is easier for the practitioner to move actuator 20 through resistance assembly 24 in the first direction than in the second direction.

Moreover, resistance assembly 24 provides sufficient frictional resistance to any internally-arising restorative forces that would tend to move distal region 16 towards neutral (e.g., spring forces arising when pull wire 23 is placed in tension via the movement of actuator 20 in the direction of arrow A). In this regard, resistance assembly 24 can also be regarded as a self-locking assembly for catheter 10.

Figure 4:
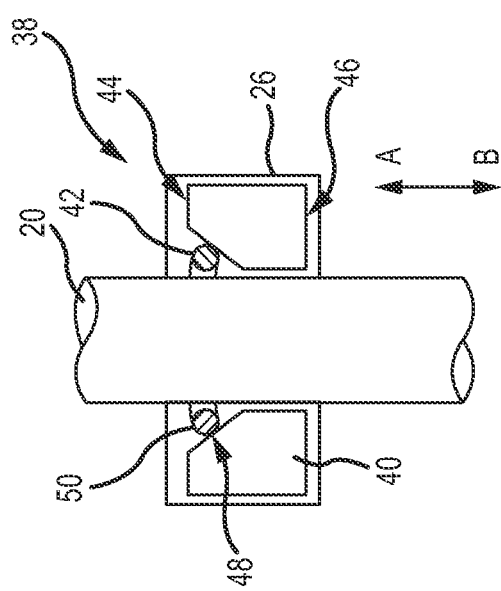
FIG. 4 is a cross-sectional view of a second exemplary embodiment of a resistance assembly according to the teachings herein.

FIG. 4 depicts a second exemplary resistance assembly 38 positioned adjacent actuator 20. Resistance assembly 38 likewise includes constraining housing 26, and further includes an annular friction assembly of an annular disk 40 and a compressible member, such as o-ring 42, about actuator 20.

Like compression ring 28, annular disk 40 includes a first surface 44 and a second, opposite surface 46; first surface 44 includes a beveled/wedge-shaped edge 48 that results in the formation of a cavity 50, while second surface 46 is generally flat. O-ring 42 is positioned adjacent first surface 44 (e.g., riding on beveled/wedge-shaped edge 48) within cavity 50.

First surface 44 is oriented in the direction where the lower resistance to movement of actuator 20 is desired. Thus, as actuator 20 is driven in the first direction along arrow A, o-ring 42 separates from annular disk 40, thereby reducing both the normal force that o-ring 42 exerts on actuator 20 and the frictional resistance to movement of actuator 20 in the first direction. Conversely, when actuator 20 is driven in the second direction along arrow B, o-ring 42 is driven down beveled/wedge-shaped edge 48 until it pinches between annular disk 40 and actuator 20, increasing both the normal force that o-ring 42 exerts on actuator 20 and the frictional resistance to movement of actuator 20 in the second direction. As a result, it is easier for the practitioner to move actuator 20 through resistance assembly 38 in the first direction than in the second direction.

Moreover, resistance assembly 38 provides sufficient frictional resistance to any internally-arising restorative forces that would tend to move distal region 16 towards neutral (e.g., spring forces arising when pull wire 23 is placed in tension via the movement of actuator 20 in the direction of arrow A). In this regard, resistance assembly 38 can also be regarded as a self-locking assembly for catheter 10.

Although several embodiments of this invention have been described above with a certain degree of particularity, those skilled in the art could make numerous alterations to the disclosed embodiments without departing from the spirit or scope of this invention.

For example, in the embodiments described above, directionally-dependent resistance to movement of actuator 20 results from differences in the normal (and thus frictional) forces exerted upon actuator 20 depending upon the direction in which it is moving. It is contemplated, however, that the coefficient of friction between actuator 20 and the resistance assembly (e.g., resistance assembly 24 and/or resistance assembly 38) can be directionally-dependent, for example by using a material with anisotropic frictional properties within the resistance assembly (e.g., as compression ring 28, annular disk 40, or o-ring 42).

In other aspects, the surface of actuator 20 and/or the surface of the resistance assembly (e.g., compression ring 28, annular disk 40, and/or o-ring 42) includes a treatment or finish, such as fish scaling, that yields directionally-dependent frictional forces.

Such materials and/or surface treatments can be used either as an alternative to or in addition to the chamfered/beveled/wedge-shaped edges 34, 48 illustrated in FIGS. 3 and 4 and described above that yield directionally-dependent normal forces.

Likewise, o-ring 42 can be modified from a toroidal shape to further alter the normal force that it exerts on actuator 20 as actuator 20 is moved. For example, o-ring 42 can also include flattened sections, chamfers, slits, and other modifications that increase the normal force that o-ring 42 exerts on actuator 20 as actuator 20 moves in the second direction along arrow B.

As a further example, although the teachings herein are explained in the context of actuators for catheters and other medical devices, the principles can also be applied to other actuators, including, for example, electronic and/or hydraulic linear actuators.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A medical device, comprising:
   a body having a proximal end and a deflectable distal region;
   a handle attached to the proximal end of the body, the handle including an actuator movable relative to the handle along a longitudinal axis thereof; and
   a resistance assembly positioned adjacent the actuator, wherein the resistance assembly exerts a first dry frictional force on the actuator when the actuator is moved in a first direction along the longitudinal axis of the handle and a second dry frictional force on the actuator when the actuator is moved in a second direction along the longitudinal axis of the handle,
   wherein the second direction is opposite the first direction, and
   wherein the second dry frictional force is greater than the first dry frictional force.

2. The medical device according to claim 1, wherein the resistance assembly comprises an annular friction assembly positioned around the actuator.

3. The medical device according to claim 2, wherein the annular friction assembly is made of a material having anisotropic frictional properties.

4. The medical device according to claim 2, wherein the annular friction assembly comprises a compression ring having a chamfered first surface and a second surface opposite the first surface, and wherein the first surface is oriented in the first direction.

5. The medical device according to claim 2, wherein the annular friction assembly comprises:
an annular disk having a beveled first surface and a second surface opposite the first surface, wherein the first surface is oriented in the first direction; and
an o-ring positioned adjacent the first surface of the annular disk.

6. The medical device according to claim 5, wherein the o-ring has a non-circular cross-sectional shape.

7. The medical device according to claim 2, wherein the resistance assembly further comprises a constraining housing, and wherein the annular friction assembly is positioned within the constraining housing.

8. The medical device according to claim 1, further comprising a pull wire extending through the body,
wherein the pull wire is coupled to the distal region of the body to effect deflection thereof,
wherein moving the actuator in the first direction effects deflection of the body from neutral in a first deflection direction.

9. The medical device according to claim 8, wherein moving the actuator in the second direction effects deflection of the body from neutral in a second deflection direction.

10. A medical device, comprising:
an elongate body having a proximal end and a deflectable distal region;
a handle coupled to the proximal end of the elongate body and including an actuator movable relative to the handle; and
a resistance assembly adjacent the actuator, wherein the resistance assembly is configured to exert a force on the actuator that varies according to a direction in which the actuator is moving relative to the handle and the resistance assembly.

11. The medical device according to claim 10, wherein the force exerted by the resistance assembly is lower when the actuator is moving relative to the handle in a direction that effects deflection of the distal region of the elongate body from neutral and higher when the actuator is moving relative to the handle in a direction that effects return of the distal region of the elongate body towards neutral.

12. The medical device according to claim 10, wherein the force exerted by the resistance assembly is lower when the actuator is moving relative to the handle in a direction that effects deflection of the distal region of the elongate body from neutral in a first deflection direction and higher when the actuator is moving relative to the handle in a direction that effects deflection of the distal region of the elongate body from neutral in a second deflection direction opposite the first deflection direction.

13. The medical device according to claim 10, wherein the resistance assembly comprises a member made of a material having anisotropic frictional properties.

14. The medical device according to claim 10, wherein at least one of a surface of the actuator facing the resistance assembly and a surface of the resistance assembly facing the actuator includes a finish that yields directionally-dependent frictional forces.

15. The medical device according to claim 10, wherein the resistance assembly comprises an annular member positioned around the actuator, wherein the annular member includes a first surface and a second surface, and wherein the first surface of the annular member includes a cavity.

16. The medical device according to claim 14, wherein the resistance assembly further comprises a compressible member positioned around the actuator adjacent the first surface of the annular member and within the cavity,
wherein movement of the actuator in a first direction separates the compressible member from the first surface of the annular member, thereby minimizing resistance to movement of the actuator in the first direction, and
wherein movement of the actuator in a second direction opposite the first direction drives the compressible member against the first surface of the annular member, thereby maximizing resistance to movement of the actuator in the second direction.

17. A resistance assembly to impart resistance to movement of an actuator for a medical device, the resistance assembly comprising:
a constraining housing; and
an annular friction assembly positioned within the housing,
wherein a lower force is required to pass the actuator through the annular friction assembly in a first direction than to pass the actuator through the annular friction assembly in the second direction.

18. The resistance assembly according to claim 16, wherein the annular friction assembly comprises a material having anisotropic frictional properties.

19. The resistance assembly according to claim 16, wherein the annular friction assembly comprises an annular compression ring having a first surface and a second surface, wherein the first surface includes a cavity such that there is greater distance between the first surface of the compression ring and the constraining housing than between the second surface of the compression ring and the constraining housing.

20. The resistance assembly according to claim 16, wherein the annular friction assembly comprises:
an annular disk having a first surface and a second surface, wherein the first surface includes a wedge-shaped portion; and
a compressible member riding on the wedge-shaped portion,
such that, when the actuator is passed through the annular friction assembly in the first direction, the compressible member separates from the annular disk, and when the actuator is passed through the annular friction assembly in the second direction, the compressible member is wedged between the actuator and the annular disk.

21. The resistance assembly according to claim 19, wherein the compressible member comprises an o-ring.

22. The medical device according to claim 1, wherein the actuator is operable to deflect the deflectable distal region of the body.

* * * * *